(12) United States Patent
Lavi et al.

(10) Patent No.: US 12,408,949 B2
(45) Date of Patent: *Sep. 9, 2025

(54) MULTIPLE TRACK SYSTEM FOR POSITIONING OF BONE SEGMENTS

(71) Applicant: OrthoPediatrics Corp., Warsaw, IN (US)

(72) Inventors: Victor A. Lavi, Delray Beach, FL (US); Volus Tucker McKenna, Pittsburgh, PA (US)

(73) Assignee: OrthoPediatrics Corp., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/343,799

(22) Filed: Jun. 29, 2023

(65) Prior Publication Data

US 2024/0138879 A1 May 2, 2024

Related U.S. Application Data

(63) Continuation of application No. 17/139,777, filed on Dec. 31, 2020, now Pat. No. 11,737,786.

(60) Provisional application No. 62/955,775, filed on Dec. 31, 2019.

(51) Int. Cl.
*A61B 17/66* (2006.01)
*A61B 17/64* (2006.01)

(52) U.S. Cl.
CPC .......... *A61B 17/66* (2013.01); *A61B 17/6416* (2013.01); *A61B 17/6475* (2013.01)

(58) Field of Classification Search
CPC . A61B 17/66; A61B 17/6416; A61B 17/6475; A61B 17/6458
USPC ...................................... 606/53–59
See application file for complete search history.

(56) References Cited

U.S. PATENT DOCUMENTS

| | | | | |
|---|---|---|---|---|
| 1,997,466 | A | * | 4/1935 | Longfellow ....... A61B 17/6441 606/57 |
| 4,988,349 | A | * | 1/1991 | Pennig ............... A61B 17/66 606/57 |
| 2006/0229605 | A1 | * | 10/2006 | Olsen ................. A61B 17/6475 606/54 |

* cited by examiner

*Primary Examiner* — Eduardo C Robert
*Assistant Examiner* — Tara Rose E Carter
(74) *Attorney, Agent, or Firm* — Gerald W. Roberts; John V. Daniluck; Dentons Bingham Greenebaum LLP

(57) ABSTRACT

The present invention presents various embodiments showing combination of a body, rods, platforms and pin (or wire) clamps for the relative fixation of separated bone segment. In some embodiments there is an overall linear arrangement of the assemblies. The rods are threaded and extend lengthwise throughout a substantial portion of the length of the body. Engaged with the threaded rods are one or more moveable platforms, with each moveable platform engaging one or more pin clamps. Preferably each moveable platform includes at least one tapped (generally threaded) hole and at least one smooth through-hole in each moveable platform, so that each moveable platform engages with one threaded rod via the tapped hole but can pass freely along the other threaded rod. Each body also typically bears at least one stationary platform, generally at or near one end of the device.

20 Claims, 14 Drawing Sheets

MULTIPLE TRACK SYSTEM FOR POSITIONING OF BONE SEGMENTS

CROSS REFERENCE TO RELATED APPLICATION

This application is a continuation of U.S. patent application Ser. No. 17/139,777, filed Dec. 31, 2020, which claims the benefit of priority to U.S. Provisional Patent Application No. 62/955,775, filed Dec. 31, 2019, both of which are incorporated herein by reference.

FIELD OF THE INVENTION

The invention pertains to methods and apparatus to anchor and adjust the relative relationships of half pins or other orthopedic structures or wires inserted into bones, for their spatial support, governance, and adjustment over time, both externally and as implanted.

BACKGROUND OF THE INVENTION

Even after several recent decades of implementation and improvement, the orthopedic arts of external fixation are by no means mature. There are claims that external fixation hearkens back even to as early as Hippocrates, or to other prominent figures in the 1800s, but in modern medicine the ubiquity of external fixation is a relatively recent phenomenon. In many cases, external fixation involves not only the surgical procedures necessary to anchor the inserted structures (half pins, wires, etc.) within the affected bones or bone segments, but also the necessary engineering to determine how beneficially to stress the structures and bones and how to adjust that stress, as well as spacing of all the included equipment, over time, to achieve the desired result. External fixation is therefore a highly developed orthopedic specialty, correctly understood as a serious and exacting technology in which the finesse of the details makes all the difference in the patient outcomes.

Especially outside the arena of orthopedic specialists in external fixation, the most familiar external fixators are the "rings" used with external fixation of the extremities, and "halos" used in external fixation typically pertaining to the head and neck. These rings and halos have been gamechangers in improving the outcomes of patients needing precise bone setting and resetting and, more importantly, having bones in need of lengthening, relative repositioning, straightening, or all three. Even so, not every external fixation setting (it turns out) requires a ring or halo. Large circular external fixator structures make patient dressing and undressing difficult and require extensive modification of clothing to accommodate them, and moreover there is a psychological component to being tethered to cumbersome and scary-looking hardware—such as rings and halos—if something simpler can suffice. This need is especially acute where primarily two-dimensional, rather than three-dimensional, bone repositioning is indicated. Accordingly, a need remains for an external fixator which is simple, elegant, effective and versatile—to allow orthopedic manipulation of bones or bone fragments for optimal regrowth, realignment and healing.

SUMMARY OF THE INVENTION

Once aspect of the present invention pertains to a device for adjusting the relative positions of bone segments. The device further includes a body having a length. The device further includes a pair of rods each rotatably supported by the body, each rod generally extending the length of the body, a portion of each rod being externally threaded. The device further includes a movable carriage threadably coupled to the threaded portion of one of the rods, the carriage being adapted and configured to attach to an implantable device that is couplable to one of the bone segments. The device further includes a platform affixed to the body, the platform being adapted and configured to attach another implantable device that is couplable to one of the bone segments; wherein rotation of the one rod moves the carriage along the threaded portion of the one rod.

Another aspect of the present invention pertains to a device for adjusting the relative positions of bone segments. The device further includes a first rod having a first length, the first rod being rotatable about a first axis, at least a portion of the first length of the first rotatable rod being externally threaded. The device further includes a second rod having a second length, the second rod being rotatable about a second axis, at least a portion of the second length of the second rotatable rod being externally threaded, the second axis being parallel to the first axis. The device further includes a first movable carriage threadably coupled to the threaded portion of the first rod, the first carriage including a first coupling feature to attach to an implantable device that is couplable to one of the bone segments. The device further includes a second movable carriage threadably coupled to the threaded portion of the second rod, the second carriage including a second coupling feature to attach to another implantable device that is couplable to another of the bone segments; wherein rotation of the first rod moves the first carriage along the threaded portion of the first rod, and rotation of the second rod moves the second carriage along the threaded portion of the second rod.

Still further embodiments of the present invention pertain to a device for external fixation of bone segments that include at least a pair of spaced apart threaded rods, each having on the proximal end a corresponding gear. Preferably, each of these gears have identical tooth spacing, and further are spaced apart such that a third gear of the same tooth spacing can be positioned so as to drive each gear of the rod simultaneously.

In still further embodiments of the present invention, an external fixation assembly for the precise locating of bone segments is contemplated in which there are at least two (2) threaded rods. One threaded rod includes external threads that are right-handed. The other rod includes external threads that are left-handed.

Still further embodiments contemplate an external fixation device for the locating of bone segments in which there are at least two (2) threaded rods. The threads of the first rod have a first, narrower pitch (i.e., spacing between threads), as does the movable carriage threadably received by that rod. The other threaded rods are fabricated with external threads spaced apart by a second, wider pitch, as is the threaded hold of the corresponding moveable platform.

Still further embodiments of the present invention pertain to external fixation devices having multiple threaded rods in which the axes of the rods are parallel to one another, but with the axes being arranged in a non-linear arrangement. As one example, the body holding these rods can be in the shape of a full or partial halo, with the rods spaced around the circumference of the halo. Such embodiments contemplate at least two (2) threaded rods.

Yet further embodiments of the present invention contemplate the coupling of a moveable carriage with a threaded rod. Rotation of the rod is prevented from resulting in rotation of the carriage by appropriate means for rotational fixation. Such rotational fixation means can include a second, nonthreaded hole through which a different rod passes; or a lip or other extension of the carriage that abuts against the body of the fixation assembly. As one example, there can be a pair of abutments that are spaced apart, each being in sliding contact with a surface of the body. One such abutment will limit rotation of a carriage in one direction, and an abutment of the other contact with the body will limit rotation in the opposite direction.

Various embodiments of the present invention include a novel combination of a body, rods, platforms and pin (or wire) clamps, sometimes generally oriented in an overall linear construct. In some embodiments the body is a rigid structure having a length greater than its width and having a cutout space (a cavity or cavities) within its perimeter. The cutout space is generally empty except for the presence of two or more rods described as follows. Within the cutout space are anchored two or more preferably threaded rods which extend lengthwise throughout a substantial portion or the entire portion of the cutout within the body. Engaged with the threaded rods, furthermore, are one or more moveable platforms or carriages, with each moveable platform engaging one or more pin clamps. Some such moveable platform include at least one (threaded or otherwise adapted and configured for coupling to a platform or carriage) hole and, in some embodiments a through-hole in each moveable platform, so that each moveable platform engages with one rod via the coupling hole but can pass freely along the other threaded rod due to the through hole. In some embodiments the body can include at least one stationary platform, generally but not necessarily located at or near one end of the device. Each platform, whether stationary or moveable, preferably supports at least one pin (wire) clamp, and preferably two pin clamps. The inventive combination of body, rods, platforms and pin (wire) clamps provides an unlimited number of positions for half pins or other orthopedic pins or wires that are connected to the pin clamps and are positionally governed by the rods and platforms, as directed by the surgeon and his or her health care team.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

ELEMENT NUMBERING

Figure 1:
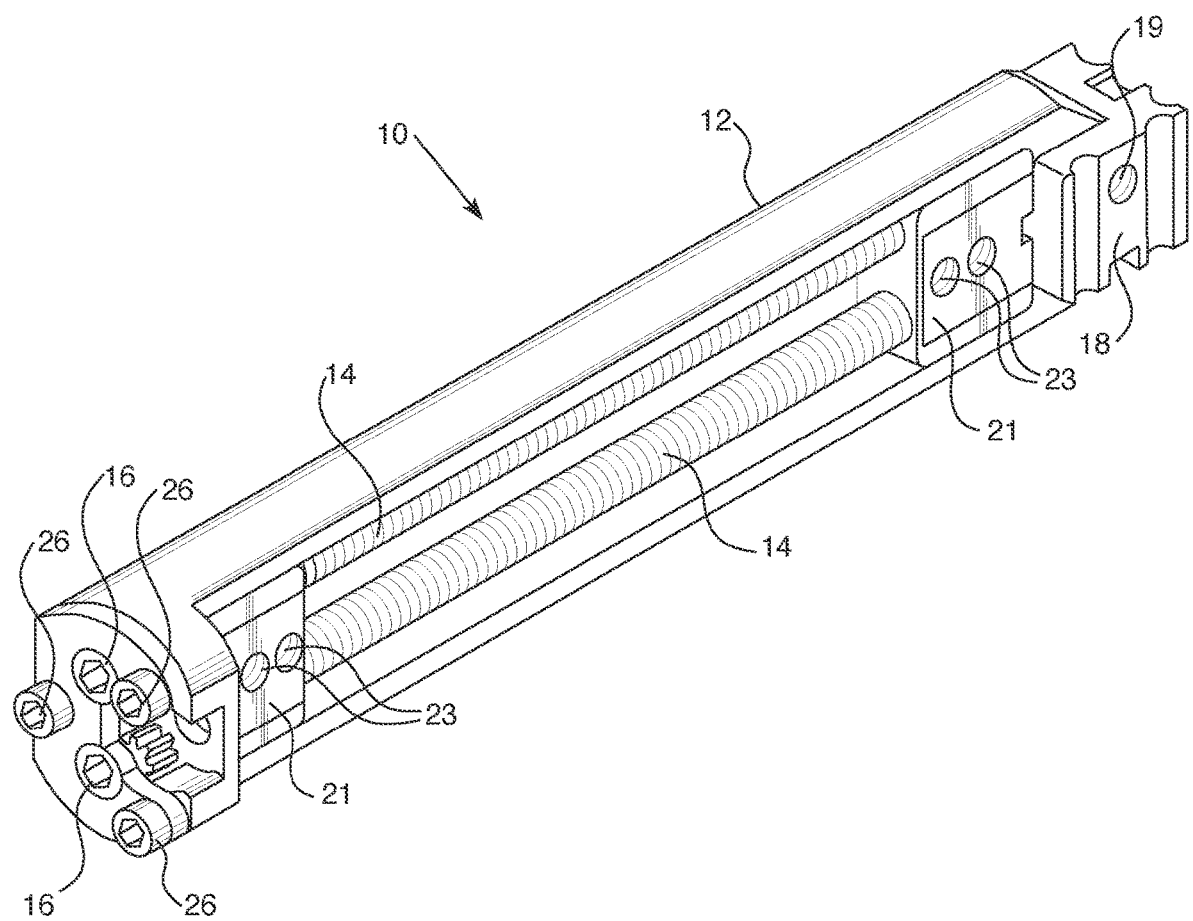
FIG. 1 is a perspective view of a dual track rail external fixator according to one embodiment of the present invention, in which two threaded rods within a body bear two moveable platforms adjacent a fixed platform at one end of the body.

The following is a list of element numbers used with all of the embodiments, and at least one noun used to describe that element. It is understood that none of the embodiments disclosed herein are limited to these nouns, and these element numbers can further include other words that would be understood by a person of ordinary skill reading and reviewing this disclosure in its entirety

| 2 | bone (tibia) |
|---|---|
| 3 | distal segment |
| 4 | defect |
| 5 | osteotomy |
| 6 | mid segment |
| 7 | proximal segment |
| 8 | pin attachment holes |
| 9.1 | transported segment |
| 9.2 | lengthened segment |
| 10 | dual track rail assembly |

-continued

| | |
|---|---|
| 12 | body |
| 14 | threaded rails/rods |
| 16 | threaded rail hex drive recess |
| 18 | fixed platform |
| 19 | fixed platform pin clamp |
| 20 | dual track rail assembly |
| 21 | moveable platform; carriage |
| 22 | body |
| 23 | pin coupling feature; clamp |
| 24 | threaded rail |
| 28 | fixed platform |
| 30 | fixed platform pin clamp |
| 32 | moveable platform |
| 34 | moveable platform pin clamp |
| 38 | external bolt |
| 40 | tool |
| 300 | dual track rail assembly |
| 302 | body |
| 304 | threaded rods |
| 306 | stacked fixed platform; carriage |
| 308 | stacked fixed platform pin clamp |
| 310 | stacked moveable platform |
| 312 | pin clamp |
| 316 | external bolt |
| 400 | device |
| 416 | threaded rail hex drive recess |
| 426 | external bolt |
| 600 | dual track rail assembly |
| 700 | dual track rail assembly |
| 800 | dual track rail assembly |
| 900 | tool |
| 902 | rotating shaft |
| 910 | gear |
| 1000 | gear |
| 1100 | gear mechanism tool |
| 1110 | gear |
| 1120 | tool guide |
| 1200 | gear |
| 1300 | dual track rail assembly |
| 1320 | body |
| 1340 | threaded rail |
| 1380 | stacked fixed platform |
| 1387 | stacked moveable platform; carriages |
| 1385 | pin clamp |
| 1389 | pin clamp |
| 1401 | external bolt |
| 1403 | external bolt |
| 1405 | half pin |
| XX01 | fastener |
| XX05 | half-pin or wire |
| XX12 | body |
| XX13 | end plate |
| XX14 | threaded rails/rods |
| XX15 | guide for gear tool |
| XX16 | threaded rod hex drive |
| XX17 | gear for threaded rod |
| XX20 | multiple track rail assembly |
| XX22 | body |
| XX28 | fixed platform |
| XX30 | pin clamp |
| XX32 | movable platform; carriage |
| XX33 | threaded hole |
| XX34 | pin clamp |
| XX35 | clearance hole |

DETAILED DESCRIPTION OF THE INVENTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "various embodiments" or "preferably," refers to features and aspects that are present in at least one embodiment, but which are optional for some embodiments, it therefore being understood that use of the word "preferably" implies the term "optional.".

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

In some embodiments, the present invention includes a body, rails, platforms that move independently from one another and pin clips on the platforms. The platforms and pin clips, taken together and when moveable, form carriages, and the carriages can move closer or further away from one another, along a preferably linear path, providing the versatility of various embodiments of the present invention in the external fixation of half pins or wires. In some embodiments of the present invention the device includes one or more fixed platforms with at least one pin clip thereon. Some embodiments include a moveable platform has both at least one tapped hole as well as at least one through hole, so that when (for example) two moveable platforms are installed adjacent one another on two threaded rails, one threaded rail governs the position of one of the moveable platforms (via its tapped hole) and the other threaded rail controls the position of the other moveable platform (through its tapped hole, on the opposite side). Using straightforward external tools, therefore, the user can reposition each moveable platform independently of a second (or further) moveable platform, making it possible for the orthopedist to manipulate half pin (or wire) positions at will, generally perpendicularly along a single linear path. For stability, each platform typically bears two half pins, but the invention embraces the possibility that only a single half pin is used per platform. While FIG. 1-13, discussed below, identify stationary and moveable platforms which generally provide pin clamps for positioning at right angles relative to the platforms, still further embodiments pertain to platforms adapted and configured to contain securable, rotating components to allow rotational variability of orientation of the pin clamps and the pins, in turn. This concept will be even more apparent after consideration of the details of FIGS. 1-13.

Figure 2:
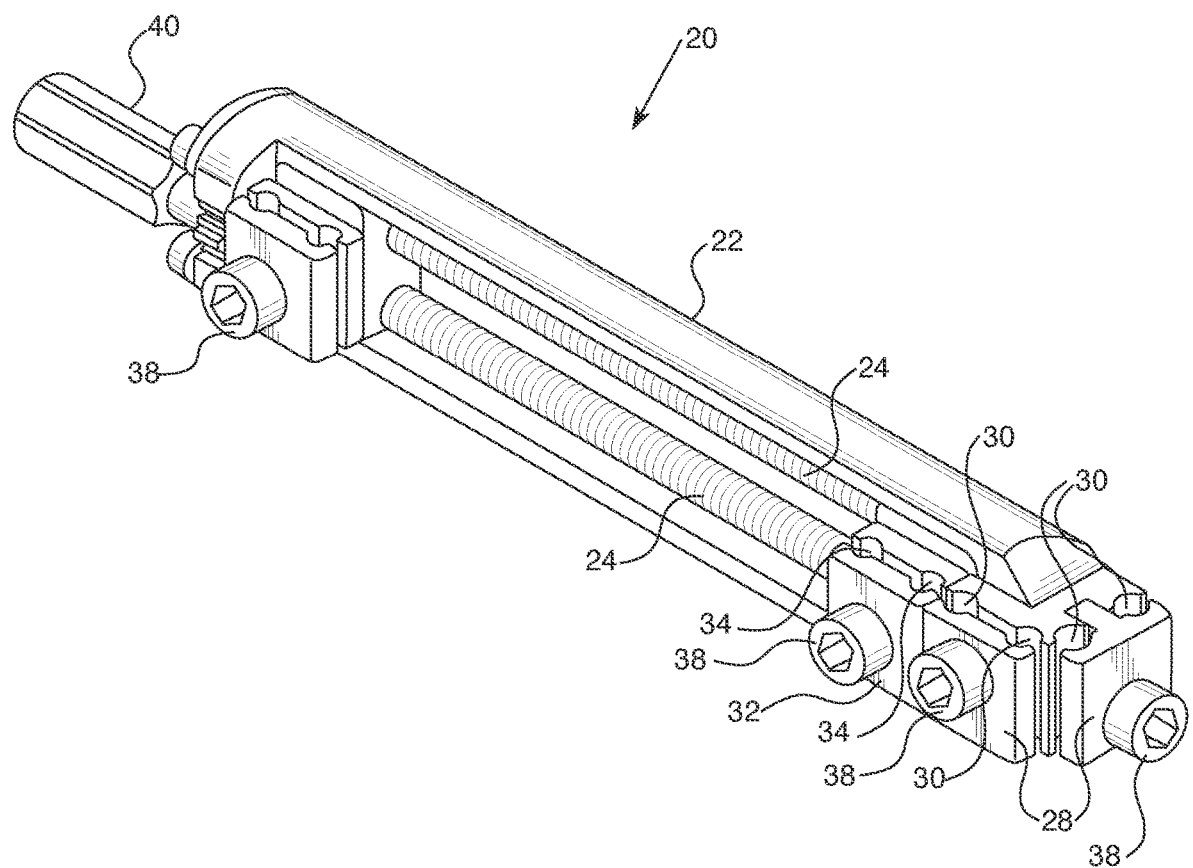
FIG. 2 is a perspective view of the device of FIG. 1, except showing the other end of the fixator and showing a tool in place at the left side of the drawing.

Referring now to FIG. 1, a dual track rail 10 according to one embodiment of the present invention includes a body 12 which contains therein two threaded rails 14 as illustrated. At the left-hand end of the device as shown in FIG. 1, two rail hex drive recesses 16 allow for manipulation of the threaded rods 14, so as to independently rotate the threaded rods 14 in either direction as desired or needed. At the right-hand side of FIG. 1, a fixed platform 18 contains a fixed platform pin clamp 19. Two moveable platforms 21 "ride" on both of the threaded rails 14, with each moveable platform 21 having a tapped hole and a through hole so that only one of the threaded rails 14 engages and drives a correspondingly threaded moveable platform 21. Accordingly, each moveable platform 21 can move independently of the other moveable platform 21 as governed by the rotation of its associated threaded rod 14 and as governed by a tool (not shown) engaged within the respective threaded rail hex drive recess 16. The pin coupling features 23 are designed to releasably couple to or hold half pins or wires used to engage bone or bone segments, so that the carriages 21 control the relative position of the half pins and, by extension, the relative positions of the bones or bone segments, during orthopedic treatment and healing. In some embodiments coupling feature 23 is a threaded hole. Yet other embodiments contemplate any manner of pin or wire fixation, such as a bayonet coupling on both the feature 23 and on the end of pin or wire Referring now to FIG. 2, it is possible to see how the platforms, whether stationary or moveable, are in some embodiments constructed of two cooperating plates, so that facing indentations in the cooperating plates create the associated coupling features or pin clamps in the platforms. FIG. 2 therefore illustrates a dual track rail assembly 20 having a body 22, threaded rails 24, individual fixed platforms 28 with fixed platform pin clamps or coupling features 30 and also moveable platforms 32 that include moveable platform pin clamps or coupling features 34. When facing plates creates the pin clamps 30 and 34, an external bolt 38 provides variable compression. A tool 900 or 1100 may be used in association with a gear 910 to drive the threaded rails 14. This gear mechanism is shown in greater detail in additional drawings, discussed later.

Figure 3:
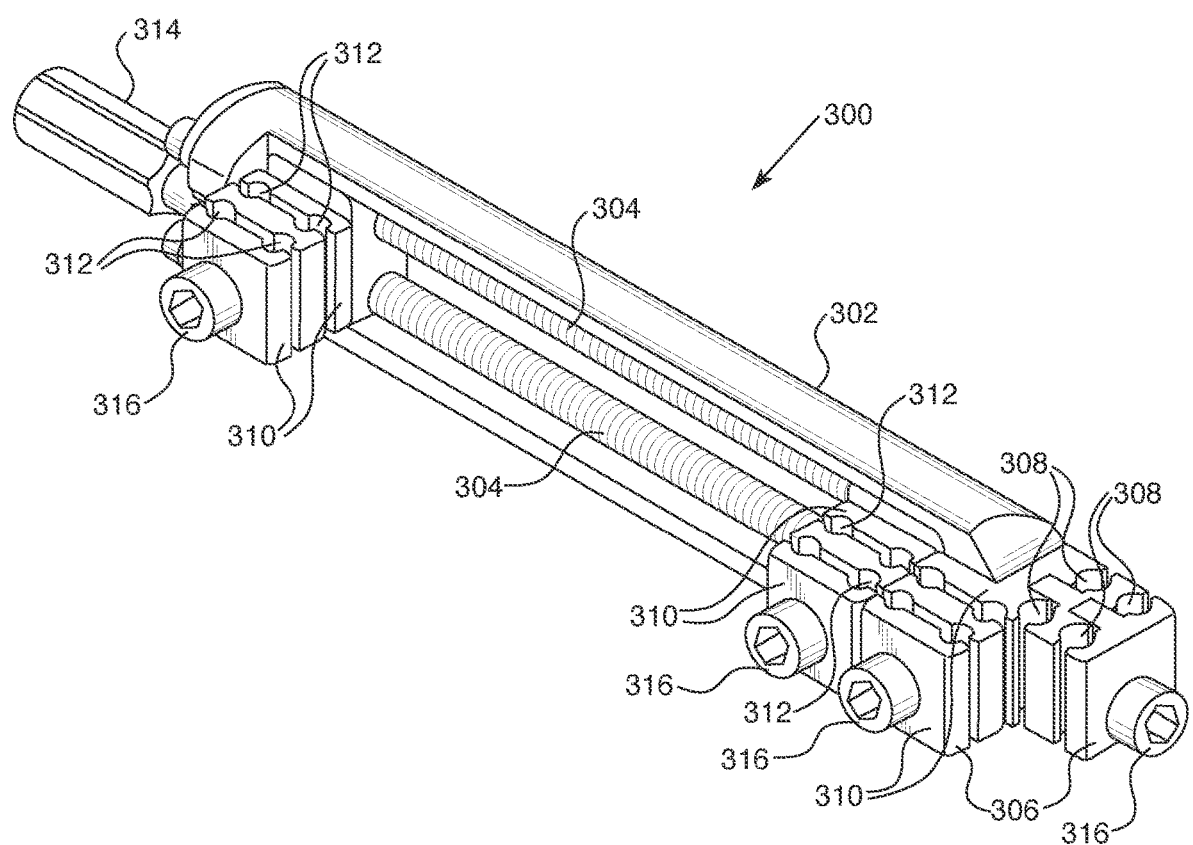
FIG. 3 is a perspective view of a device of FIG. 1, except in which both the stationary and moveable platforms are stacked.

Referring now to FIG. 3, not only is it feasible for platforms to be made up of two facing plates, but such two-plate platforms (or the platforms 21) can be stacked, so as to provide additional pin clamp positions to hold and move half pins or wires for external fixation. In FIG. 3, the dual track rail assembly 300 contains a body 302 which bears two threaded rods 304, as shown. Stacked moveable platforms or carriages 310 are positioned along the length of assembly 300 by rotation of the corresponding rod 304. The base of each lowermost plate of each platform 310 is preferably fitted with both a tapped hole and a through hole, so that different moveable platforms are governed by the rotation of different threaded rods 304. As shown in FIG. 3, a stacked carriage can be constructed as a "sandwich" of first or bottom plate with at least one coupling feature or indentation on one face, a second middle plate with similar features on opposing faces (with one of the opposing faces also being opposite of the coupling feature of the first plate), and a third or top plate with a similar coupling feature on a face that is opposite of the other opposing face of the middle plate. Although indentations are shown and described, it is understood that the coupling features may be of any type that provide for fixation of the pin or wire to the carriage. Stacked fixed platforms 306 and stacked fixed platform pin clamps 308 are shown in configurations analogous to those of FIGS. 1 and 2. External bolts 316 provide variable compression needed to create securing force within the pin clamps 308 and 312.

Figure 4:
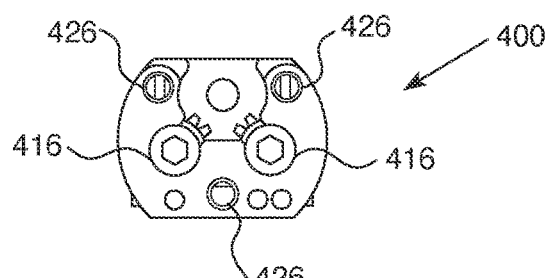
FIG. 4 is a side elevational view of the end face of the device shown at the left side of FIG. 1.
Figure 5:
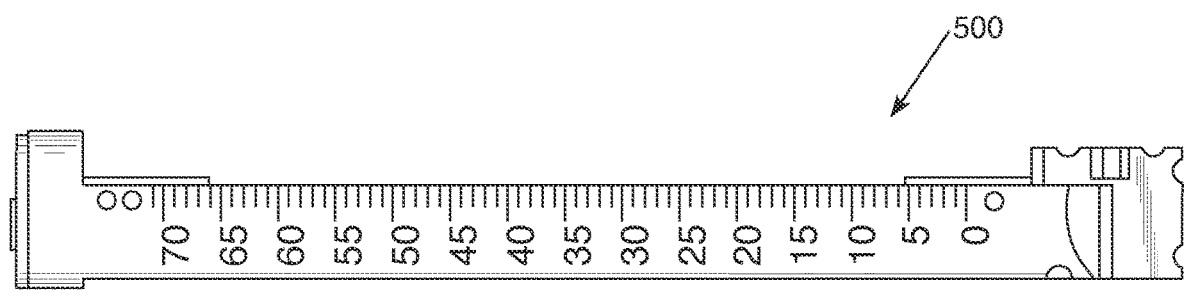
FIG. 5 is a side elevational view of one side of the device of FIG. 1.
Figure 6:
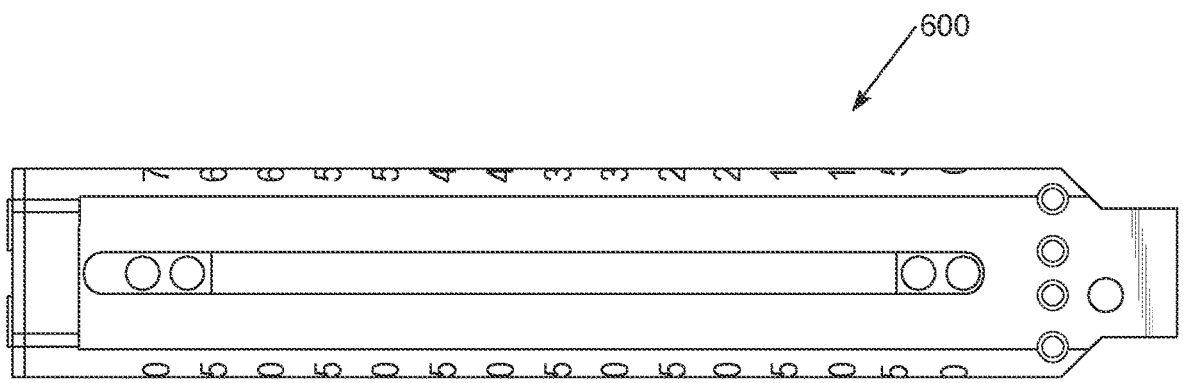
FIG. 6 is a side elevational view of the side of the device of FIG. 1 opposite the side that bears the stationary and moveable platforms.
Figure 7:
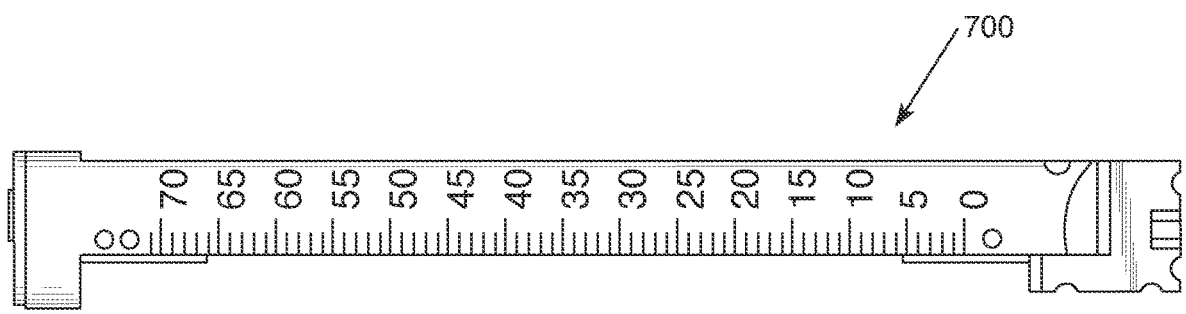
FIG. 7 is a side elevational view of another side of the device of FIG. 1.

FIG. 4 illustrates an end elevational view of an embodiment of the invention, depicting the device 400 having thereon two threaded rail hex drive recesses 416 and three external bolts 426 for use in engaging an optional external gear mechanism (not shown). FIGS. 5-8 show representative side elevation views of the various faces of embodiments of the invention, provided with ruler markings or other indicia for ease of use when establishing pin spacings. These device reference numerals are 500, 600, 700 and 800, respectively. It should be appreciated that, as the ruler marking numbers span somewhat over/around respective generally cylindrically convex faces of the dual track rail assembly 600, those respective ruler marking numbers are only partially visible in the side plan view of FIG. 6.

Figure 8:
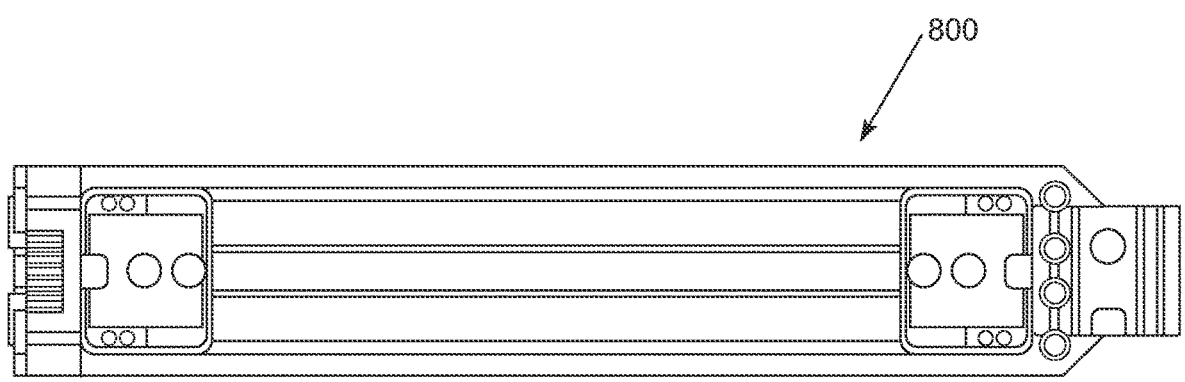
FIG. 8 is a top plan view of the device of FIG. 1.

FIG. 8 is a top plan view of a dual track rail assembly, and showing various features as previously discussed with regards to assemblies 10, 20, and 300.

Figure 9:
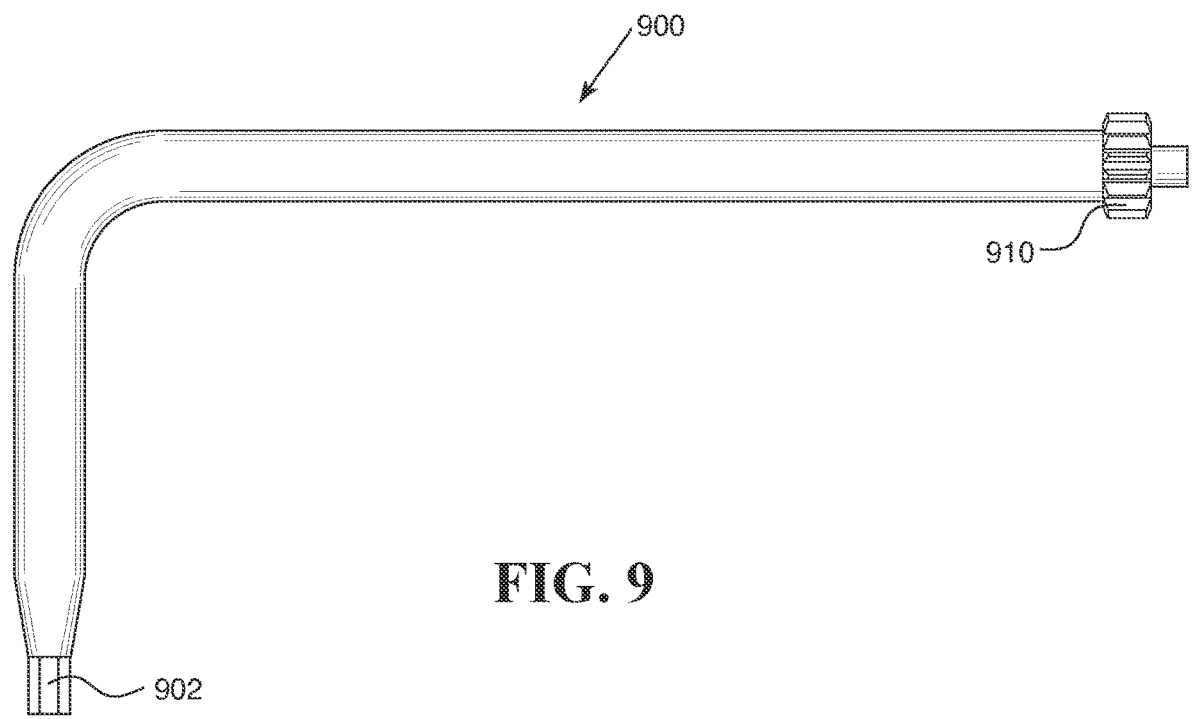
FIG. 9 is an optional gear mechanism tool for use with the device of FIG. 1.
Figure 10:
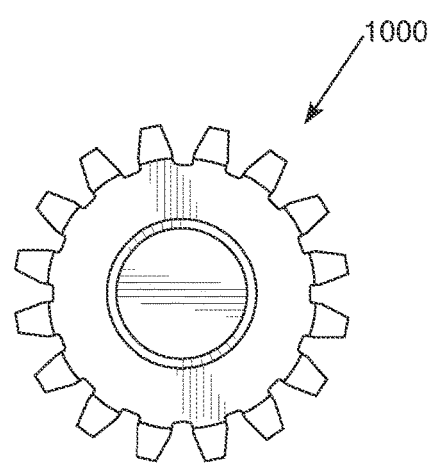
FIG. 10 is a side elevational detail of the gear of the tool of FIG. 9.
Figure 11:
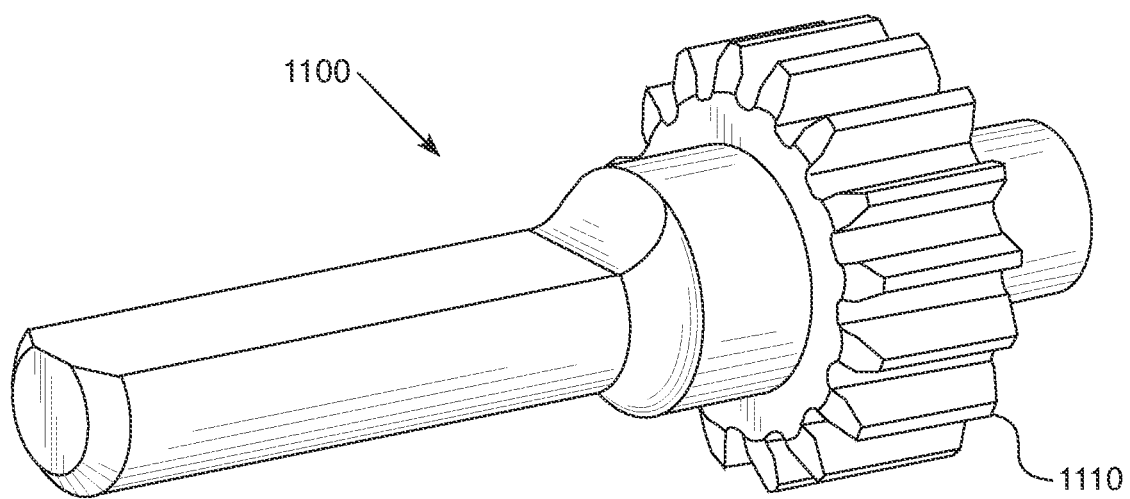
FIG. 11 is an alternative embodiment of the optional gear mechanism tool of FIG. 9.
Figure 12:
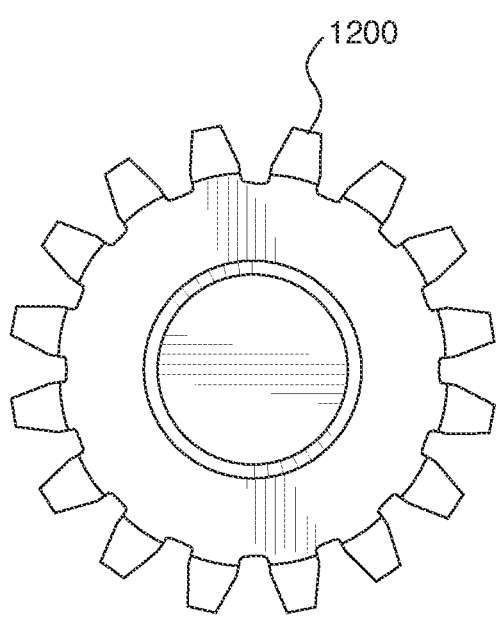
FIG. 12 is a side elevational detail of the head of the tool of FIG. 11.

FIG. 9 is a side elevational view of an embodiment of the optional external gear mechanism identified above, with the tool 900 having a rotating shaft 902 therein which includes a gear 910. FIG. 10 shows the gear 910 of FIG. 9 in sectional view as gear 1000. FIG. 11 depicts an alternative embodiment of the optional gear add-on of the present invention, in which the gear mechanism tool 1100 bears gear 1110 thereon. The gear 1110 of FIG. 11 is shown in sectional view as gear 1200 in FIG. 12.

Figure 13:
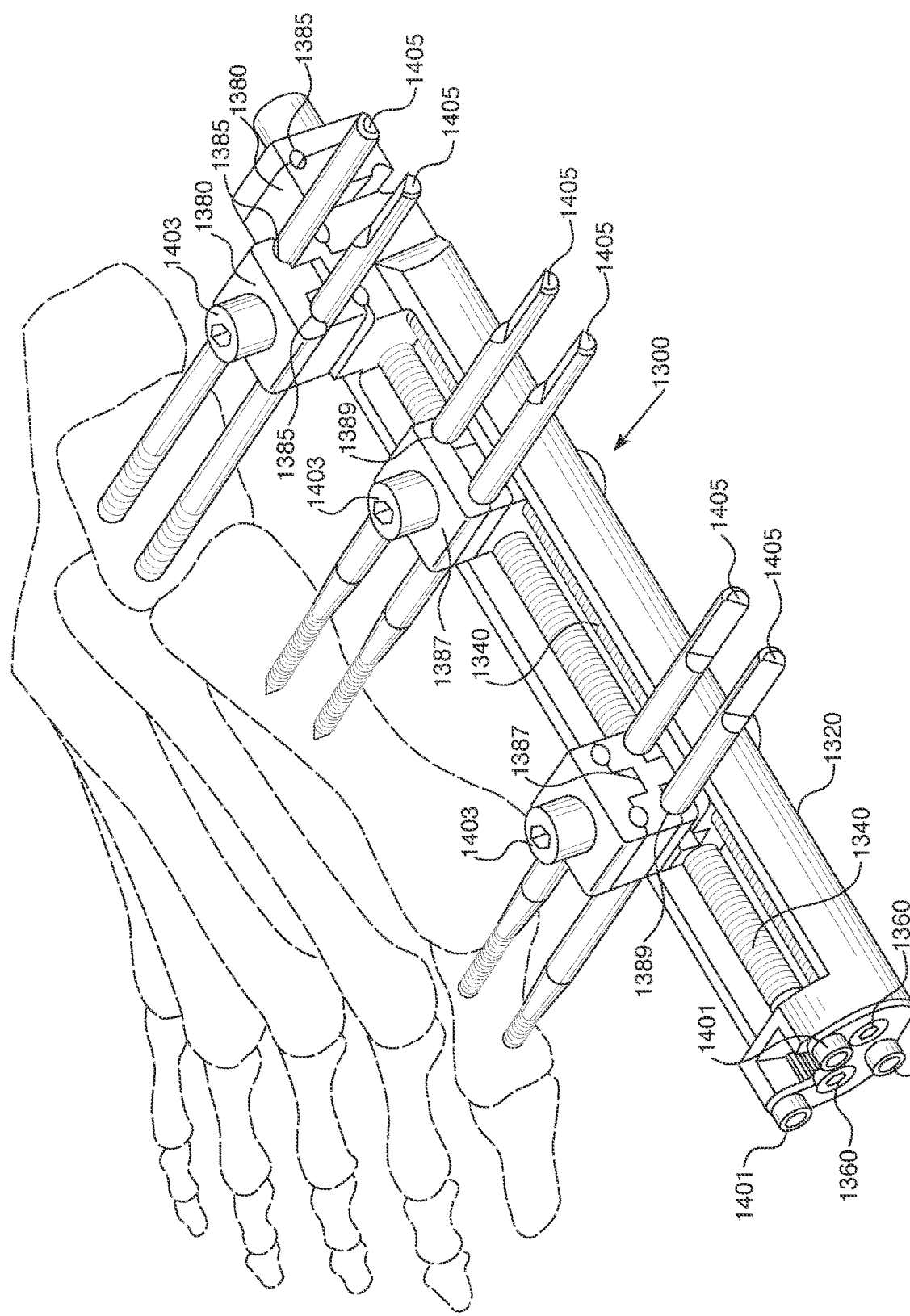
FIG. 13 is a plan view of a device according to another embodiment of the present invention, shown with six half pins in place in adjacent bones of a patient's foot, illustrating the variability of not only placement and suspension of the half pins but also the ability externally to adjust the positioning of the half pins as the bone repositioning and healing process takes place.

Finally, synthesizing many of the features of the present invention is the drawing of FIG. 13.

FIG. 13 illustrates the dual track rail device 1300, having a body 1320 and threaded rails 1340, analogously to all previous applicable FIGS. As in FIG. 3, the platforms are stacked and are either stacked fixed platforms 1380 or stacked moveable platforms 1387. The platforms bear pin clamps 1385 and 1389 as shown, to engage half pins (known in the art) for insertion into bone or bone segments to be treated (as shown in dotted lines). External bolts 1403 provide compression to frictionally or otherwise couple half pins 1405 in their respective pin clamps 1385, 1389, and external bolts 1401 for an optional gear mechanism are present at one end of the device.

Various Embodiments of the present invention permit multiple external fixation half pins can be oriented and secured in any number of positions. Some embodiments having at least two half pins per platform (carriage) provide dimensional stability, although yet other embodiment contemplate the use of one-half pin. Preferably, from at least one end of each rail, any rail can be turned independently by means of its associated hex drive recess discussed above. By moving the desired rail, the practitioner can move the associated platform, that is, the combined platform and at least one pin clamp that together form a functional carriage for half pins or other orthopedic wires. When one of the optional gear devices is engaged with the end bolts, turning the gear can move two or more platforms simultaneously, thereby maintaining any predetermined distance between them.

It is important to note that, although a typical "dual track rail" has two rails, as shown in the figures, yet other embodiments pertain to devices including three, four or more rails—and also stacking rails rather than placing them side by side. Gear tools may be adapted to move two or more rails—such engineering being well within the ordinary skill of the art. Rails can be preassembled with all the same thread direction, typically clockwise threads, but the rails can be preassembled with opposite thread directions or the rods may be devised with counterclockwise threads, all depending on the clinical application to be addressed. Those embodiments including a fixed platform provides the use with a third position relative to which one or two more moveable platforms may translate in space, increasing the half pin capacity of the device without having all platforms be moveable.

As described above, although the platforms of FIGS. 1-13 show right angle position of pin clamps on generally flat platforms, yet other embodiments contemplate affixing rotationally versatile pin clamps of various types on the moveable platforms, to give a range of angle adjustment (relative to the threaded rods) of the half pin to be secured between the affected bone and the present device. FIGS. 14-19 are discussed in the following paragraphs. These paragraphs utilize a numbering convention of XXYY-Z, in which XX represents the embodiment (15, 16, or 18), YY represents a specific element, and -Z refers to a particular threaded rod (−1, −2, −3, or −4). It is understood that the element limitations YY are common among these figures, and still further are similar or the same as the same two-digit extension used in any of the preceding drawings 1-13 as will be recognized by persons of ordinary skill in the art.

Figure 14:
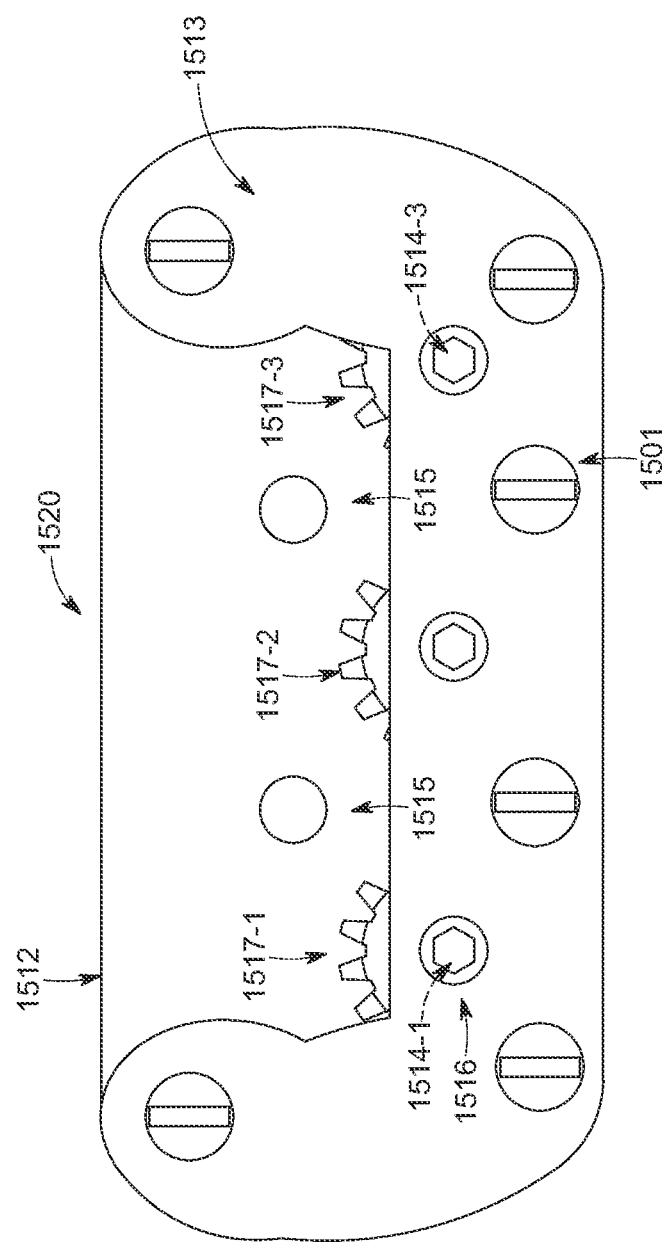
FIG. 14 is an end view of a schematic representation of a triple track assembly according to another embodiment of the present invention.

FIG. 14 shows an end view of a triple track rail assembly 1520 according to one embodiment of the present invention. External fixation assembly 1520 includes a body 1512 that rotatably supports three (3) preferably parallel actuating rods 1514-1, 1514-2 (in the middle) and 1514-3. The dashed line indications of FIG. 14 indicate that these actuating rods are hidden in FIG. 14 but are generally coaxial with the corresponding actuating rod hex drive 1516. In some embodiments, each of the actuating rods includes a threaded exterior. Various embodiments contemplate threaded rods that are all threaded in the same direction (i.e., right-handed or left-handed), or combinations of the two hands of threading. Various embodiments of the present invention contemplate any type of pitch (i.e., thread spacing) for the rod external threads. For example, a bone segment that will be transported relatively large distances may be provided with a coarser pitch. However, those threaded rods associated with bone segments that benefit from relatively small movements may have a finer (narrower) pitch.

FIG. 14 shows that the end of each rod XX16 is preferably but not necessarily coupled to a gear XX17, such as a spur gear. As shown, rod 1514-1 includes a gear 1517-1, as an example. These threaded rods can be turned by turning the corresponding gear XX17, instead of turning the corresponding hex drive XX16. This rotation can be achieved using the tools 900, 1000, 1100, or 1200, as previously discussed. These tool gears are adapted and configured to mesh with the rod and the gear XX17, simply by holding the tool in meshing contact with the rod and the gear, and rotating the tool. In that manner, rods XX14 can be moved independently of one another. However, in some embodiments of the present invention the body 1512 includes one or more holes 1550 (which can be through holes or blank holes). As shown on FIG. 14, one of the hole guides 1515 is preferably equally spaced apart from adjacent rod end gears 1517-1 and 1517-2. By inserting the dowel pin end of tools 900 or 1100, the corresponding tool gear (910 or 1110) will mesh with each of the adjacent gears 1517-1 and 1517-2. Therefore, turning of the installed tool by the user will result in simultaneous rotation of each threaded rod 1514-1 and 1514-2, with subsequent translational movement of the corresponding moveable carriage 1532-1 or 1532-2 (carriages not shown). FIG. 14 shows a second hole 1515 that is spaced for meshing contact of the tool gear with rod end gear 1517-2 and 1517-3.

Figure 15:
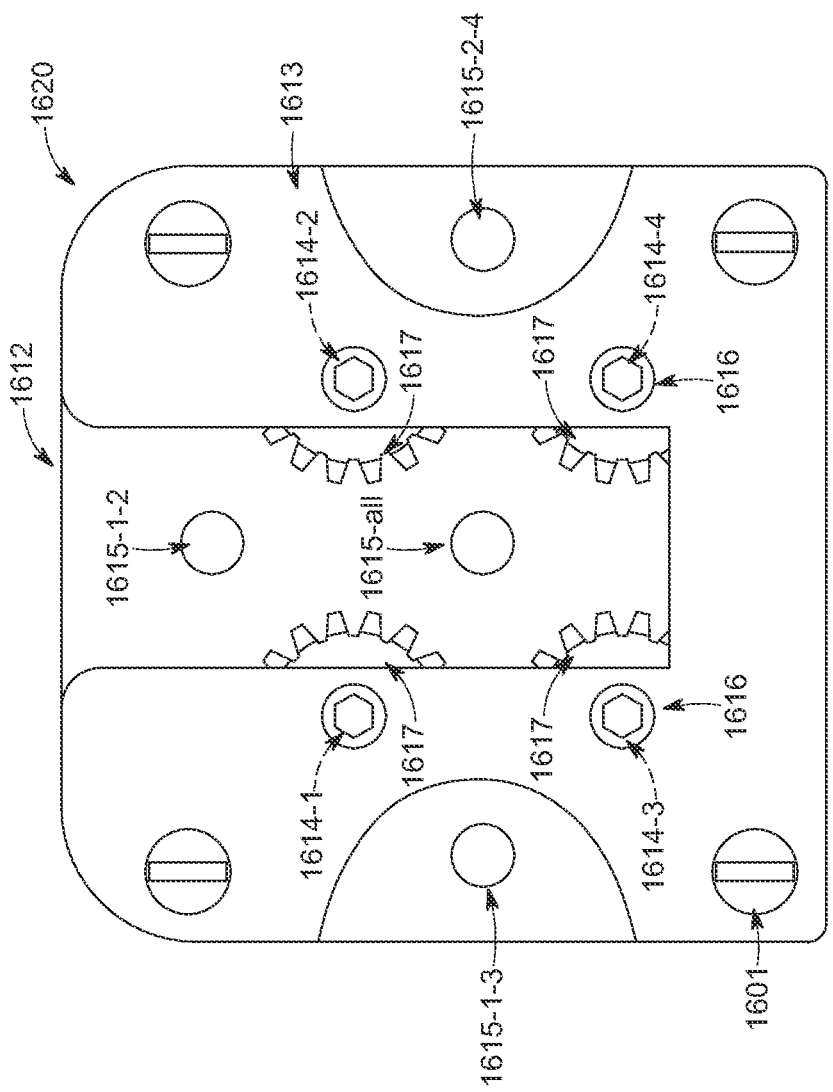
FIG. 15 is an end view of a schematic representation of a quad track assembly according to another embodiment of the present invention.

FIG. 15 is an end view of a schematic representation of a quad track rail assembly 1620 according to another embodiment the present invention. Those of ordinary skill in the art will recognize that various features of assembly 1620 are similar to or the same as the corresponding features discussed above for assembly 1520, or to other assemblies shown herein. In one embodiment, a body 1612 provides rotational support for four (4) actuating rods 1614, shown arranged in a 2×2 (square) configuration.

However, yet other embodiments of the present invention contemplate quad rail assemblies with the actuating rods located adjacent to one another, such as that shown for assembly 1520. However, it is understood that for assemblies having four fixation assemblies having multiple rods that the rods can be arranged relative to one another in any fashion. For example, the three rods 1514 could be arranged in a non-linear manner (such as a V arrangement), and further the spacing of the rotational axes of the rods, although shown equidistant, can be of any spacing (such as with two rods being closer to one another than a different pair of rods). Likewise, the assembly 1620 showing four (4) actuating rods is one embodiment, but it is understood that yet other embodiments contemplate spacing of the rod rotational axes that is not equidistant (i.e., not the square configuration shown in FIG. 15), and further nonlinear. As one example, the four rods 1614 could include an upside-down V configuration, a right side up V configuration, a zig-zag configuration, or any other.

One difference between apparatus 1620 and apparatus 1520 is the number of locations through which tool gears can be used for the simultaneous rotation of multiple gears. For example, FIG. 15 shows a first guiding feature 1615—all that is located centrally and equally spaced from all four gears 1617. By using one of the tools 900 or 1100 described herein, that one tool when guided to rotate about this central location 1615—all will simultaneously rotate all four gears 1617. Located above that guiding hole 1615—all is another guiding hole 1615-1-2. The use of a gear tool guided at this location will result in simultaneous rotation of shafts 1614-1 and 1614-2. In similar fashion, the use of a gear tool that rotates about the location hole 1615-2-4 will simultaneously rotate rods 1614-2 and 1614-4; likewise, the use of a gear at guided location 1615-2-3 will simultaneously rotate rods 1614-1 and 1614-3. A still further gear location can be located toward the bottom of apparatus 1620 for the simultaneous rotation of actuating rod 1614-3 and 1614-4.

Figures 16A, 16B:
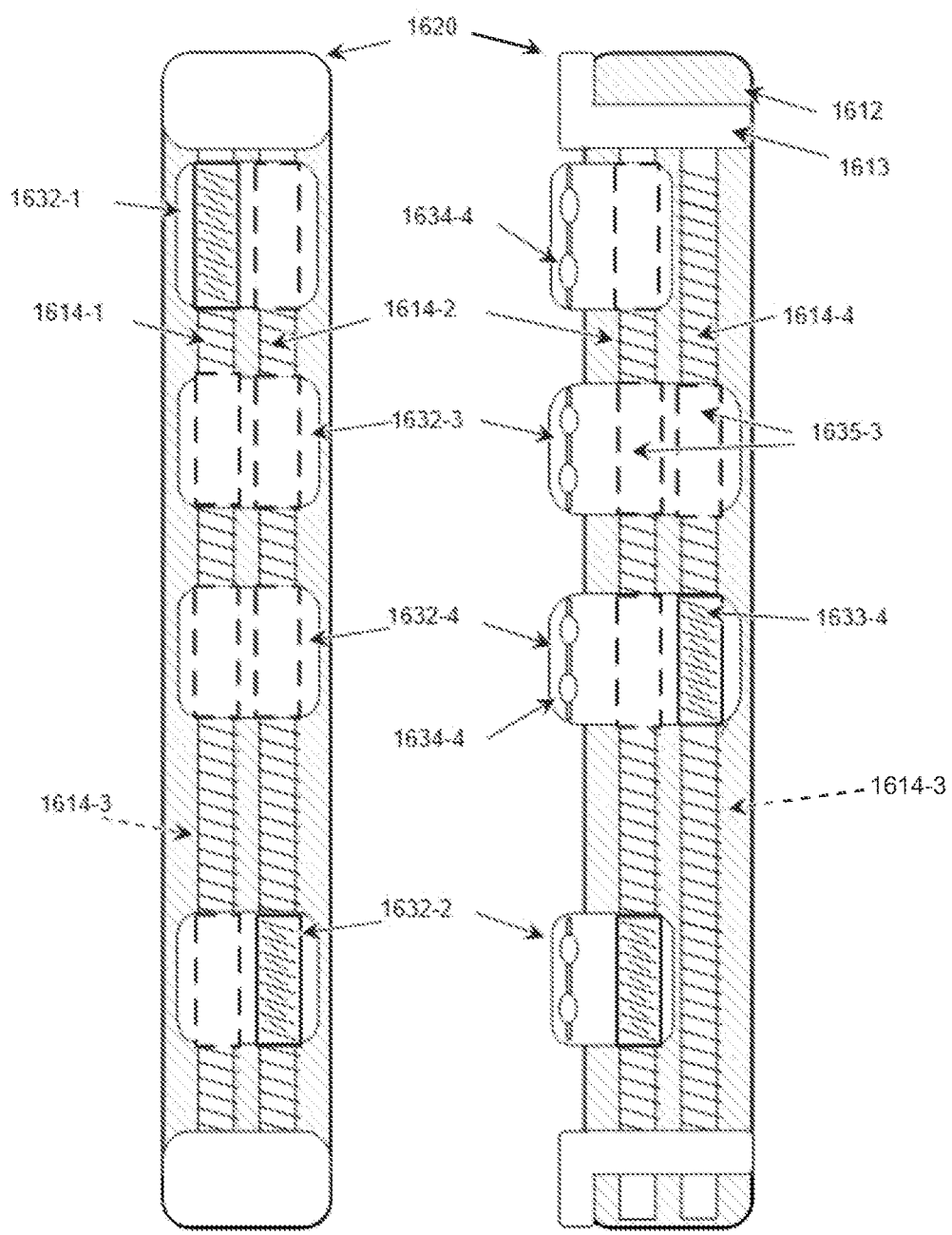
FIG. 16A is a top plan schematic representation of the apparatus of FIG. 15.
FIG. 16B is an orthogonal view of the apparatus of FIG. 16A.

FIGS. 16A and 16B show top and side schematic representations, respectively, of quad rail assembly 1620. For the sake of simplicity, FIG. 16B does not show the side of body 1522 so that the bottom row of actuating rods can be shown. Further, as another example, the gears and other features shown in FIG. 15 are not represented in either FIG. 16A or 16B.

FIGS. 16A and 16B show the length of the four rods (which in this embodiment are all generally equal), which are further roughly the same length as the body 1612. Each of the actuating rods 1614 includes threaded portions, as shown. Note that rod 1614-3 does not appear in either of these figures, this rod being below rod 1614-1 and hidden by rod 1614-4.

Four (4) movable carriages 1632 are shown. Each one includes a through hole 1633 that is threaded for mating contact with the external threads of the associated rod. Referring to FIG. 16B, it can be seen that carriage 1632-4 includes a single threaded rod 1633-4 that threadably couples to actuating rod 1614-4. In some embodiments, carriage 1632-4 includes three other clearance holes, one each permitting the passing therethrough of a corresponding rod 1614-1, 1614-2, or 1614-3. Likewise, each of the platforms 1632 include a single threaded hole for threaded engagement with a single actuating rod. However, although carriages 1632 are shown and described having three additional clearance holes 1635, yet other embodiments of the present invention contemplate fewer clearance holes, thus corresponding to no contact with one or more of the actuating rods. Referring to carriages 1632-1 and 1632-2, it can be seen that each of them includes a single threaded hole and a single clearance hole. Neither of these two carriages are in contact with actuating rod 1614-3 or 1614-4.

In some embodiments, the use of a threaded hole and at least one corresponding through hole (for passage of a threaded rod) provides for rotational fixation of the carriage, such that rotation of the threaded rod provides only translational movement of the corresponding carriage. Without some support to prevent rotational motion, the rotational movement of a rod could result in rotation of the carriage about the rotational axis of the rod. As shown and described, the spaced apart support provided by a rod extending through a clearance hole prevents the carriage from rotating. However, in yet other embodiments, the carriage includes only a threaded hole, and further includes means for preventing rotation of the carriage. Referring to FIGS. 16A and 16B, it can be seen that carriage 1632-2 could be coupled only to rod 1614-2 with an external surface of the carriage maintaining sliding contact with either or both of the body 1612 or an adjacent threaded rod. With regards to body contact, it would be possible to provide two (2) vertically spaced apart locations (referring to FIG. 16B), one of which would prevent all but limited rotation in one direction, and all but limited rotation in the other direction, by coming into interfering contact with a surface of the body. It is further contemplated in some embodiments that the interior of a carriage such as 1632-2 (and referring now to FIG. 16A) include a curving concave surface that is in sliding contact with the major diameter of the threads of rod 1614-1. In that case, contact of this concave surface at the top would prevent all but limited rotation one direction, whereas contact with the bottom area of the curved surface would prevent all but limited rotation in the other direction.

The carriages 1632 of FIGS. 16A and 16B are schematically shown with either threaded holes (XX33) or clearance holes (XX35). Referring to carriage 1632.1, it can be seen in FIG. 16A that the threaded hole 1633-1 is graphically represented by an interlacing of long lines and short lines, representative of the threaded coupling of the rod external threads and the carriage internal threads. Carriage 1632-1 further shows the representation of a clearance hole 1635-1 in both FIGS. 16A and 16B. The clearance hole XX35 is represented by broken lines, with a view of the threaded rod omitted for purposes of clarity. It is further understood that FIGS. 16A and 16B do not show rod 1614-3, which is otherwise located behind either rod 1614-1 or 1614-4, respectively.

Figure 17C:
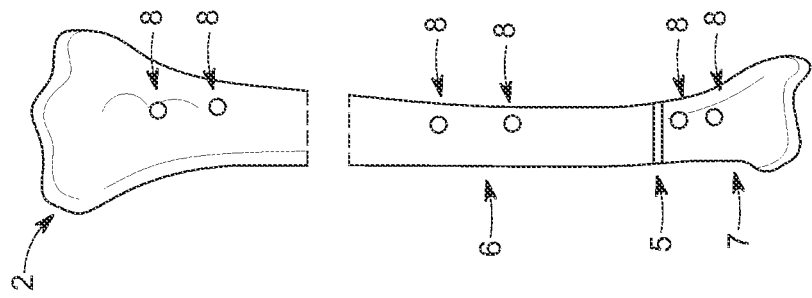
FIG. 17C is a schematic representation of the tibia of FIG. 17B showing holes in different bone segments of the tibia for placement of half pins or wires.
Figure 17B:
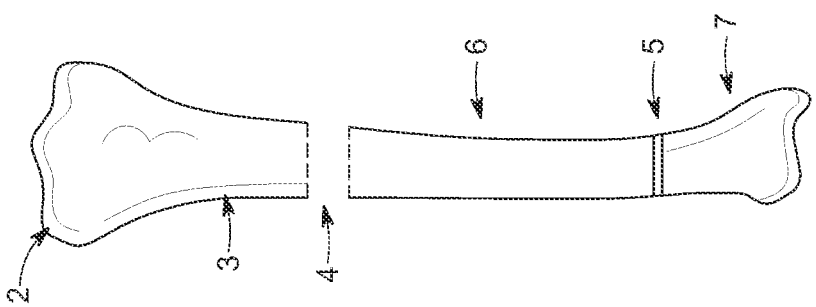
FIG. 17B is a schematic representation of the tibia of FIG. 17A and showing the location of an osteotomy cut.
Figure 17A:
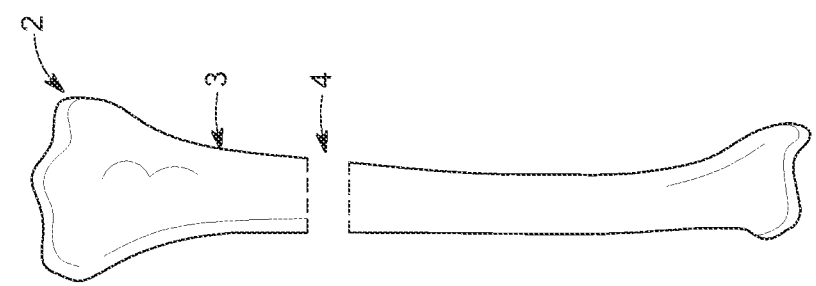
FIG. 17A is a schematic representation of a tibia with a bone defect.

FIGS. 17A, 17B, and 17C show various preparations made to a tibia. FIG. 17A shows that a bone defect (such as a tumor or other) has been removed from the tibia. FIG. 17B shows the location of the tibia where an osteotomy is to be performed on the tibia, thus separating the tibia into a distal segment 3, mid segment 6, and a proximal segment 7. FIG. 17C shows a pair of attachment locations that have been prepared on the bone segments 3, 6, and 7.

Figure 18:
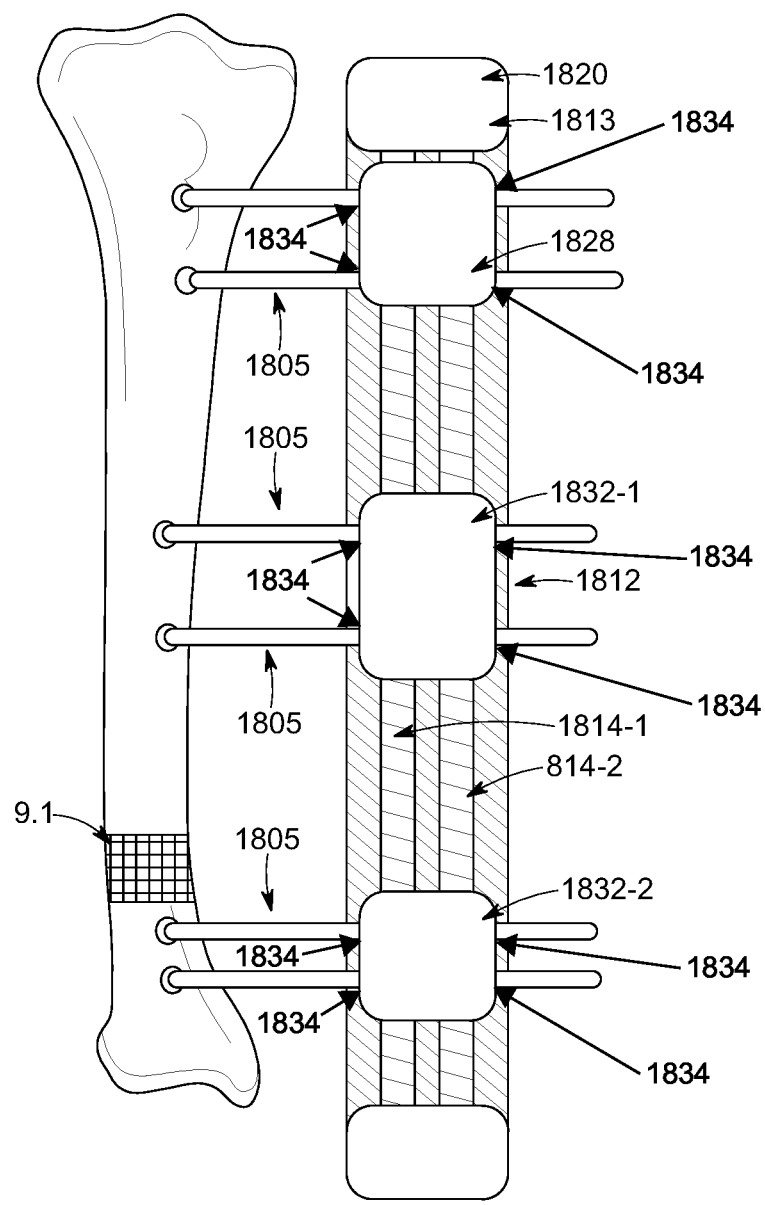
FIG. 18 is a top schematic representation of a dual track assembly according to another embodiment of the invention, with half pins attaching the assembly to the tibia of FIG. 17C.

FIG. 18 shows the tibia of FIG. 17C that has been surgically attached to a dual track rail assembly 1820 according to one embodiment of the present invention. As shown, assembly 1620 includes a fixed platform 1828 that is fixed in a static position relative to body 1812. A first moveable carriage 1832-1 is threadably engaged with a first actuating rod 1814-1, and a second moveable carriage 1832-2 is threadably connected to a second threaded actuating rod 1814-2. As discussed previously, rods 1814 can be rotated by either the rod hex end or the rod end gear (now shown in FIG. 18). In order to rotate the rod and cause the corresponding moveable carriage to translate along the length of the corresponding rod. In some embodiments, apparatus 1820 (shown schematically) is located external to soft tissue surrounding the tibia. However, in yet other embodiments, a multiple track rail assembly XX20 can be adapted and configured for implantation within the soft tissue surrounding the tibia.

Assembly 1820 is shown interconnected to the tibia by implants 1805. These implants (such as pins, half pins, wires, cables, or the like) are attached to either platform 1828 or one of carriages 1832 by way of pin clamps 1834. Referring briefly to FIG. 16B, it can be seen that in some embodiments the platforms or carriages include a separable cover that can be held in place by one or more fasteners to the body of the platform or carriage (as shown and discussed with regards to FIG. 1, FIG. 2, FIG. 3, or shown attached to pins in FIG. 13). The implantable devices 1805 can be held in a fixed relationship relative to the platform or carriage in any suitable manner.

FIG. 18 represents one point in the corresponding medical procedure. Referring again briefly to FIG. 17C, pins 1805 of carriage 1832-2 were implanted into the locations 8 of segment 7. The pins 1805 of carriage 1832-1 were located at the attachment locations 8 of middle segment 6. Rod 1805 of fixed platform 1828 were implanted into the locations 8 of distalmost bone segment 3.

After coupling of implants 1805 to a tibia, the procedure of establishing a growth area 9.5 begins. In one embodiment of the procedure, the proximal end mid bone segments 7 and 6, respectively, are gradually separated such that osteogenesis occurs in a region 9.1 between segments 7 and 6, at the location of the osteotomy. During this procedure, segments 3 and 7 are held in relative fixed locations. Mid segment 6 is gradually moved as the osteogenesis progresses, until coming into contact with the end of the distal segment 3. In this manner, the section 9.1 of new growth is about the same as the defect 4 that was removed, with the result being that the tibia of FIG. 8 (at the end of the procedure) is about the same length as the original tibia with a defect.

Figure 19:
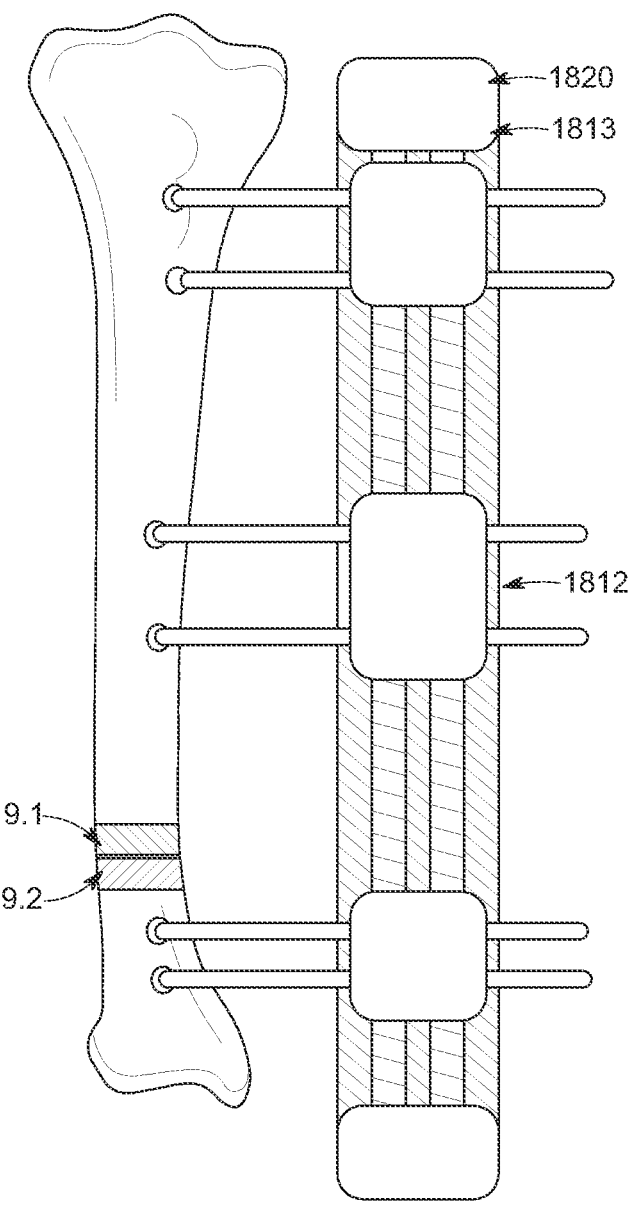
FIG. 19 is a top schematic representation of a dual track assembly according to another embodiment of the invention, with half pins attaching the assembly to the tibia of FIG. 17C.

FIG. 19 shows the use of apparatus 1820 for a medical procedure that is different than the procedure discussed relative to FIG. 18. The device 1820 is coupled by implants 1805 to bone segments 7, 6, and 3 as shown in FIG. 17C. A first portion of this medical procedure is similar to that described with regards to FIG. 18. During this initial part of the procedure, platform 1828 and carriage 1832-2 are held in fixed relative positions. Carriage 1832-1, coupled by implants 1805 to bone mid segment 6, is gradually moved toward platform 1828 so as to grow a segment 9.1 that is about the same length as the defect 4 that was removed. After this initial phase of growth and achievement of a grown section 9.1, the overall length of the tibia is about the same as the overall length before the defect was removed.

However, in some cases, the patient may require additional lengthening of the tibia. In those cases, in a follow-on procedure, platform 1828 and carriage 1832-1 are maintained in fixed relationship to each other. However, platform 1832-2 is moved in a proximal direction (i.e., downward as viewed on FIG. 19), with the result being the achievement of a lengthened segment 9.2, such that the overall length of the tibia of FIG. 19 is greater than the length of the original tibia which included the defect. Such manipulation is achievable by apparatus 1820 because of the completely independent translational motion of one carriage XX32-Z relative to another movable carriage XX32-Z. It is understood that with regards to FIG. 19, or any of the embodiments discussed herein, that it may be appropriate to provide one of the threaded rods with right handed threads, and the other of the left handed rods with left hand threads. By so doing, the angular movement applied by the surgeon to either of the two rods is in the same direction in order to achieve a relative separation of the corresponding carriages.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

The invention claimed is:

1. A device for adjusting the relative positions of bone segments, comprising:
   a body having a length;
   a pair of rods, each of said rods rotatably supported by said body, a first of said rods including a first externally threaded rod portion longitudinally extending about a first axis, a second of said rods including a second externally threaded rod portion longitudinally extending about a second axis, said second axis being spaced apart from said first axis;
   a movable carriage threadably coupled to the threaded portion of one of said rods, said carriage being adapted and configured to attach to an implantable device that is couplable to one of the bone segments; and
   a platform affixed to said body, said platform being adapted and configured to attach to another implantable device that is couplable to one of the bone segments,
   wherein threads of the first externally threaded rod portion are laterally spaced apart from threads of the second externally threaded rod portion, wherein rotation of the one said rod moves said carriage along the threaded portion of the one said rod, and
   wherein said movable carriage includes a hole having an inner diameter greater than the major diameter of the threaded portion of the one said rod, said other rod passing through the hole.

2. The device of claim 1, wherein said movable carriage is adapted and configured to attach to two half pins, and wherein each of said half pins is couplable to one of the bone segments.

3. The device of claim 1, wherein said body is adapted and configured to prevent said movable carriage from rotating.

4. The device of claim 1, wherein said movable carriage is constrained to only translate during rotation of the one said rod.

5. The device of claim 1, wherein said movable carriage is not free to rotate during rotation of the one said rod.

6. The device of claim 1, wherein at least one of the implantable devices is a half pin, and wherein said movable carriage is adapted and configured to attach to said half pin by frictional clamping.

7. The device of claim 1, wherein at least one of the implantable devices is a half pin, and wherein said movable carriage is adapted and configured to attach to said half pin by a threaded connection.

8. The device of claim 1, wherein at least one of the implantable devices is a half pin, a wire, or a cable.

9. The device of claim 1, wherein each said rod includes a pair of opposing ends, and each of said ends is rotatably supported by said body.

10. The device of claim 1, wherein rotation of the one said rod moves said carriage relative to said platform.

11. The device of claim 1, wherein each of said rods is rotatable independently of the other of said rods.

12. The device of claim 1, wherein said platform is a first platform, and which further comprises a second platform affixed to said body, said second platform being adapted and configured to attach to a half pin that is couplable to one of the bone segments, said first platform and said second platform being spaced apart along the length of said body.

13. A device for adjusting the relative positions of bone segments, comprising:
   a first rod having a first length, said first rod being rotatable about a first axis, at least a portion of the first length of said first rotatable rod being externally threaded;
   a second rod having a second length, said second rod being rotatable about a second axis, at least a portion of the second length of said second rotatable rod being externally threaded, said second axis being spaced apart from said first axis;
   a first movable carriage threadably coupled to the threaded portion of said first rod, said first carriage including a first coupling feature, said first coupling feature being adapted and configured to attach to an implantable device that is couplable to one of the bone segments; and
   a second movable carriage threadably coupled to the threaded portion of said second rod, said second carriage including a second coupling feature, said second coupling feature being adapted and configured to attach to another implantable device that is couplable to another of the bone segments,
   wherein rotation of said first rod moves said first carriage along the threaded portion of said first rod, and rotation of said second rod moves said second carriage along the threaded portion of said second rod, and
   wherein said first movable carriage includes a threaded hole for threaded coupling to said first rod, and first movable carriage includes a first clearance hole for passage therethrough of said second rod.

14. The device of claim 13, wherein said first carriage and said second carriage maintain a fixed angular relationship during rotation of said first rod or during rotation of said second rod.

15. The device of claim 13, wherein said first rod is adjacent to said second rod.

16. The device of claim 13, further comprising:
   a body adapted and configured to rotatably support said first rod and said second rod; and
   a platform in fixed relationship to said body, said platform including a third coupling feature adapted and configured to attach to a half pin, said half pin including a portion adapted and configured to screw into one of the bone segments.

17. The device of claim 13, wherein said first rod is rotatable independently of said second rod.

18. The device of claim 13, wherein said first rod includes a first gear on one end and said second rod includes a second gear on one end, said first gear and said second gear being adapted and configured for meshing engagement with a gear of a tool.

19. The device of claim 13, wherein said first rod is threaded with one of right-hand threads or left-hand threads, and wherein said second rod is threaded with the other of said right-hand threads or left-hand threads.

20. The device of claim 13, wherein the device is adapted and configured to be implantable in a patient.

* * * * *